(12) United States Patent
Lamont

(10) Patent No.: US 6,491,654 B2
(45) Date of Patent: Dec. 10, 2002

(54) ADJUSTABLE LOCKING WEIGHT BEARING DEVICE FOR USE WITH A MEDICAL BOOT

(76) Inventor: William D. Lamont, 54283 Meadowood Ct., Shelby Township, MI (US) 48316

(*) Notice: Subject to any disclaimer, the term of this patent is extended or adjusted under 35 U.S.C. 154(b) by 0 days.

(21) Appl. No.: 09/867,862

(22) Filed: May 30, 2001

(65) Prior Publication Data

US 2001/0049484 A1 Dec. 6, 2001

Related U.S. Application Data

(60) Provisional application No. 60/209,386, filed on Jun. 5, 2000.

(51) Int. Cl.$^7$ .................................................. A61F 5/00
(52) U.S. Cl. ............................. 602/13; 602/5; 602/23; 602/27
(58) Field of Search ........................ 602/5, 13, 27–29, 602/46, 65, 20

(56) References Cited

U.S. PATENT DOCUMENTS

| 5,143,058 A | * | 9/1992 | Luber et al. ................... 602/28 |
| 5,226,245 A | | 7/1993 | Lamont ............................ 36/9 |
| 5,372,576 A | * | 12/1994 | Hicks ........................... 602/27 |
| 5,431,624 A | * | 7/1995 | Saxton et al. .................. 602/27 |
| 5,609,570 A | | 3/1997 | Lamont ......................... 602/65 |
| 5,762,622 A | | 6/1998 | Lamont ......................... 602/65 |
| 5,961,477 A | * | 10/1999 | Turtzo .......................... 602/27 |

* cited by examiner

Primary Examiner—Michael A. Brown
Assistant Examiner—Lalita M Hamilton
(74) Attorney, Agent, or Firm—Charles W. Chandler

(57) ABSTRACT

A soft medical boot mounted in a splint. A soft liquid filled cushion is disposed in the ankle portion of the boot and positioned in an adjusted position with respect to a heel opening in the boot.

8 Claims, 4 Drawing Sheets

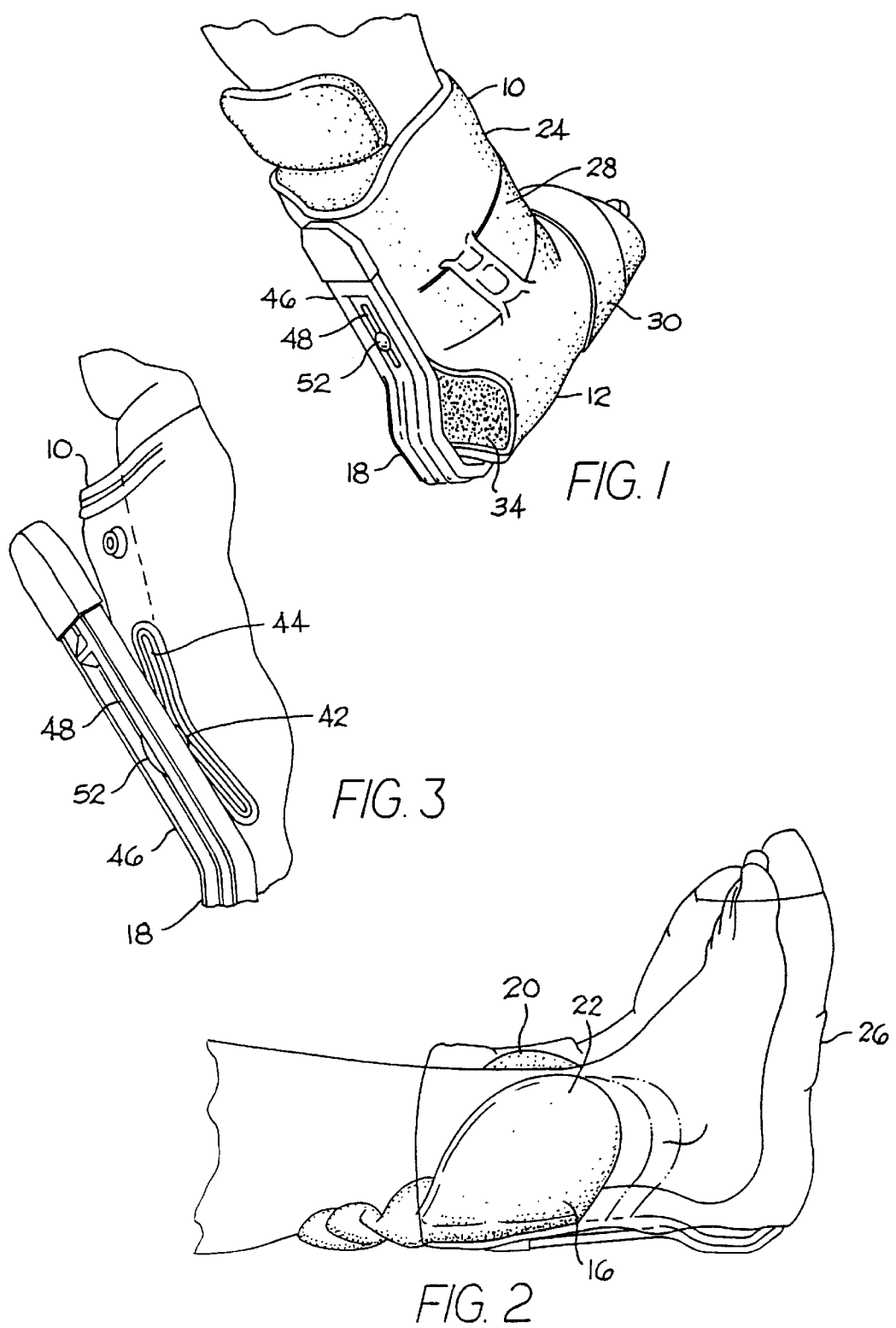

ADJUSTABLE LOCKING WEIGHT BEARING DEVICE FOR USE WITH A MEDICAL BOOT

CROSS-REFERENCE TO RELATED PATENT APPLICATIONS

This application is related to disclosure document No. DE00215, filed Jun. 22, 1999, and claims priority to Provisional Application No. 60/209,386, filed Jun. 5, 2000.

BACKGROUND AND SUMMARY OF THE INVENTION

The invention relates to medical boots, and more particularly to a height adjustment device that utilizes a weight-bearing substance, i.e. water, air, gel, foam, fluid, sand, glass beads, Styrofoam balls, plastic, paraffin, rice, wheat or any other mixture or element that gives height and/or cushioning of the lower leg.

The broad purpose of the invention is to help increase blood flow to an individual primarily at bedrest, thereby eliminating capillary closure and impedance of blood flow, and reducing tissue damage (bedsores) at the heel area and the Achilles tendon. It is ideal also for the patient at bedrest who has developed ulcerations of the lower leg (heel, Achilles tendon) from further tissue damage, by suspending various portions of the lower leg and heel while wound care healing is taking place.

Today's protocol calls for a patient in bed to be repositioned every two hours as a standard of care. To date, no other commercially-available product is known to me that offers a boot configuration, with or without a right angle splint, with a weight-bearing substance and a locking feature that can be adjusted to a number of prescribed exact locations, in a very simplified matter by the caregiver every two hours as recommended.

When using the invention with a splint, the positioning locations are graphically displayed on the splint material. Numerals can be used or other means for indicating increments of measure. I prefer to use a numerical system for ease of operation. A chart will be developed to aid in calculating the distance between the various positions.

A measurement system can be used at the back of the boot, or the inside or outside of the boot on any plane of the boot surface.

This invention includes a slotted area on the rear of the boot, preferably with a heat-fused radius, for visualizing the pressure relief of the lower leg and foot. A mechanical splinting device with a weight-bearing device can be used either internally or externally in a boot-type configuration.

Splinting material, in conjunction with a weight-bearing device can also be used in a horizontal, vertical or any other plane to achieve adjustability.

The splinting material utilizes three locking nubs to hold a snap cap in place. Other stops could also be utilized (i.e. a pin and hole device, a nub and groove device, buttons, Velcro, screws, or any other mechanical force that would meet a counterforce that gives a stationary positioning means).

A weight-bearing substance for relieving pressure to the lower leg and heel can be achieved without a splinting device, with a locking attachment to the weight-bearing device using a material that encircles the foot and/or a portion of the leg, and having a slotted area or a series of holes, which can receive the locking device. The material that encircles the foot or leg portion can be made from foam, lamb's wool, sheepskin, Kodel or laminated materials. The locking device can be manufactured by other manufacturing means (i.e. die cufting, sewing, wire burning, hot melting, punching, etc.) to create an opening to receive a partial or full locking device that enables a weight-bearing material to be positioned for reducing pressure to the lower leg and foot.

To achieve a locking adjustable weight-bearing device without a splint, the invention utilizes a snap cap with a socket, and a hook and loop material that locks the weight-bearing material to the cap socket, while the hook material engages to the hook compatible boot configuration, and locks it at the desired position (1, 2, or 3).

Still further objects and advantages of the invention will become readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which:

FIG. 1 is a perspective view of a boot assembly illustrating the invention;

FIG. 2 is a view illustrating how relocating the boot cushion adjusts the support of the cushion under the patient's leg;

FIG. 3 is an enlarged view showing how the splint is attached to the boot;

DESCRIPTION OF THE PREFERRED EMBODIMENT

Figure 10:
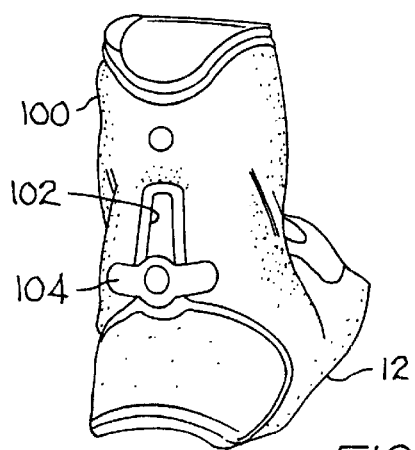
FIG. 10 is a perspective view showing the splintless form of the invention.

A preferred boot assembly 10 is illustrated in FIG. 1. Another embodiment of the invention is illustrated in FIG. 10, at 100. In both cases, the preferred device includes a soft boot 12.

Referring to FIG. 1, boot assembly 10 includes an insert (cushion) 16, and a splint 18.

Boot 12 is of the type generally illustrated in my U.S. Pat. No. 5,226,245, issued Jul. 13, 1993, to William D. Lamont for "Protective Boot Structure". Insert 16 (cushion) is similar in configuration to the cushion illustrated in my U.S. Pat. No. 5,609,570 issued Mar. 11, 1997, for "A Protective Medical boot and Orthotic Splint". It has a pair of side panels or wings 20, 22, and an internal core of a flexible compressible sac of a gel material. The cushion is also illustrated in my U.S. Pat. No. 5,762,622 issued Jun. 9, 1998 for "Medical Boot with Unitary Splint".

A splint similar to splint 18 is illustrated in my U.S. Pat. No. 5,762,622.

The boot has an upper leg portion 24 and a sole 26. The boot is formed from a single multi-layer sheet containing the profile of the leg portion and the sole. The sole is formed from edges that are stitched together in a seam extending from the heel to the toe of the boot.

The boot material is an elastomeric-shaped retaining material, such as a soft, flexible compressible open cell urethane, foam core, with an outer layer of an ultra smooth, soft, non-allergenic cloth, such as brushed tricot. A continuous layer of small loops characterizes this fabric, which makes the material compatible with fabric hook fastener means, such as Velcro fasteners. The entire outer cover, including both the upper portion of the boot and the sole has a brushed tricot covering so that a patch of a fabric hook material can be connected in any position on the boot exterior.

The entire edge of boot 12 above the sole is heat fused and compressed together and cut to the boot configuration, all in one process.

The boot has a cooperating leg strap 28 and a foot strap 30. The boot has a heel opening 34, which receives the splint and provides air circulation to the heel area.

Figure 4:
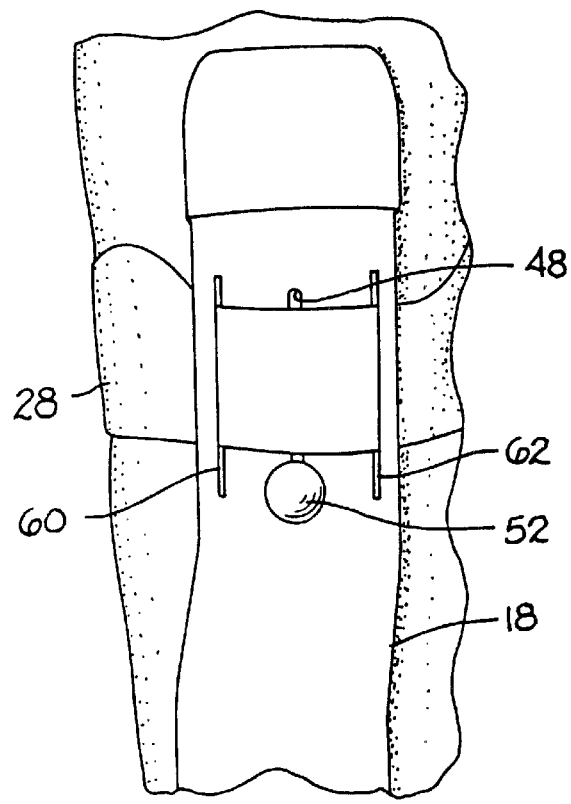
FIGS. 4 and 5 are other views showing the splint attached to the boot.
Figure 8:
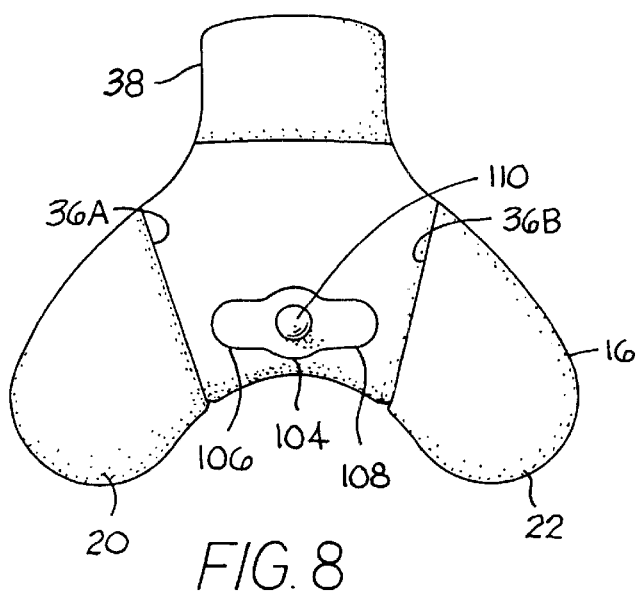
FIGS. 8 and 9 are views illustrating the cushion.
Figure 9:
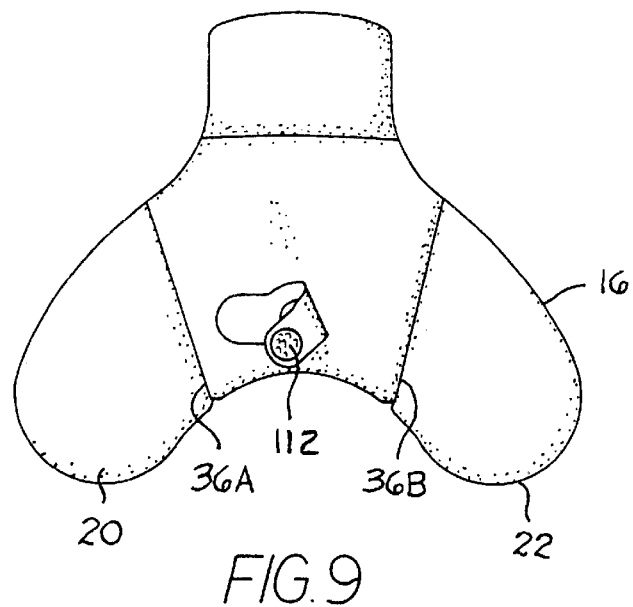

The cushion is illustrated in FIGS. 8 and 9 and is similar to the configuration disclosed in my prior U.S. Pat. No. 5,609,570, see FIGS. 4 and 5, col.5, lines 51–67; and col. 6, lines 1–20, incorporated herein by reference. The cushion has the same material construction as the remainder of the boot, that is, with an inner core of a flexible, compressible urethane foam and an outside covering of a brushed tricot material. The central portion of the cushion has a somewhat rectangular configuration while the side panels 20 and 22 fold along the side edges of the central panel and extend at about a 45° angle from a pair of parallel fold lines 36A and 36B.

The central portion of the cushion has an internal recess, not shown, housing a fluid-tight plastic container filled with an air, water, and gel combination. The cushion has a top panel 38 which folds down along a fold line 40 and is formed of the same material as the remainder of the cushion.

Referring to FIG. 3, the cushion has a male snap 42 located on the rear of the central panel and aligned with a slot 44 along the rear of the ankle portion of the boot. The slot is about halfway between the heel opening and the top of the boot and is about 3" long and ¾" wide, with a heat fused and stitched edge. The slot is generally rectangular in configuration.

The rear leg 46 of the splint has a longitudinal slot 48. When the splint is inserted in the boot, the slot in the splint is aligned with slot 44 in the cushion. The snap on the cushion is engaged with a female snap 52 carried in the slot of the splint. The female snap is on the inside of the splint and has a head on the outside of the splint.

Figure 5:
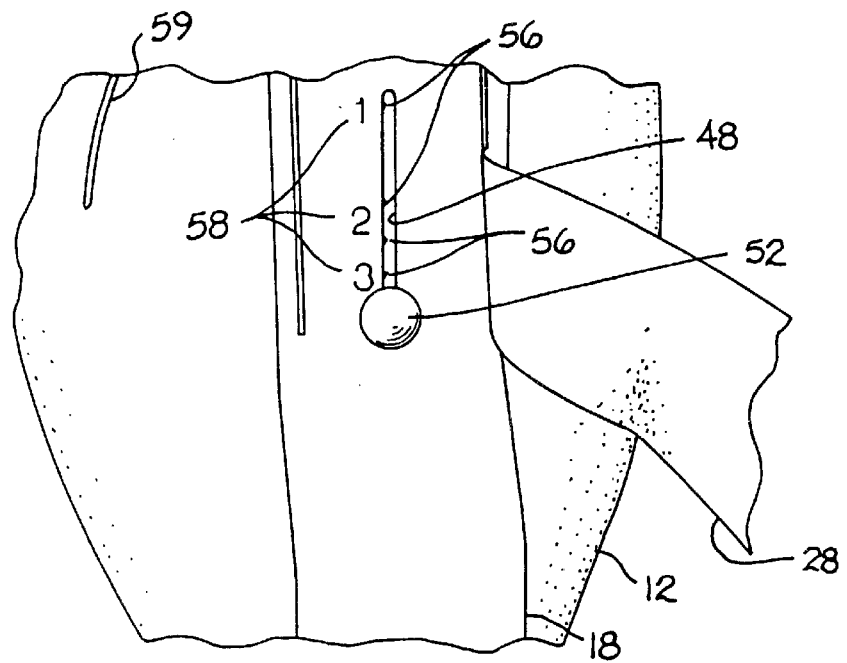
Figure 6:
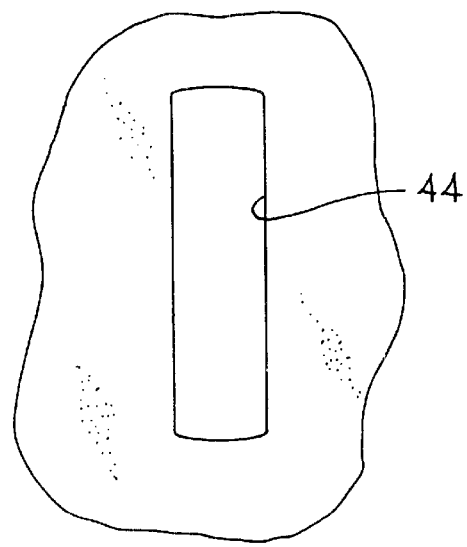
FIGS. 6 and 7 illustrate the splintless form of the invention.
Figure 7:
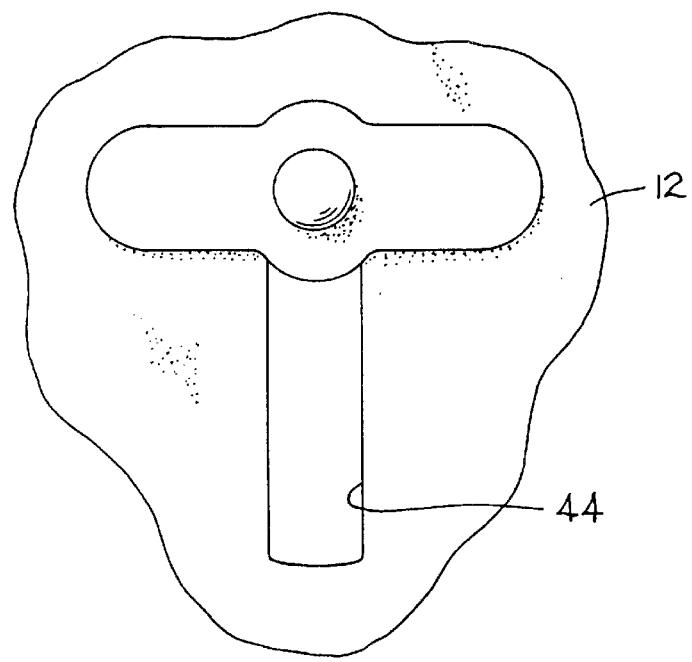

Referring to FIG. 5, the head is slidable up and down, that is, lengthwise in slot 48. The head has a neck that is slightly narrower than the slot in the splint. A series of nubs 56 on one side of the slot provide an obstruction to the head in such a manner that the head can be positively positioned in three positions designated by the indicia 58. Thus, when the head is connected to the cushion, the position of the cushion with respect to the foot portion of the splint can be adjusted as illustrated in FIG. 2. This, in turn, permits adjusting the location of the patient's leg and heel in the splint.

Leg strap 28 extends through a pair of openings 59 in the boot on opposite sides of the slot and also is threaded through a pair of slots 60 and 62 in the splint to securely locate the splint with respect to the boot.

FIG. 10 illustrates another embodiment 100 of the invention that does not employ a rigid splint. In this case, the boot is formed with a slot 102 that is identical in length and configuration to that of the embodiment of FIG. 1. Referring to FIGS. 8 and 9, a fabric flexible retainer 104 having a pair of wings 106 and 108 with a female snap 110 is connected to the male snap on the cushion. Each wing has a fabric hook-type fastener 112 that is engageable with the outside surface of the boot material. When the cushion has been located a desirable distance from the heel well, the two wings are pressed against the surface of the boot to form a fastening means for locating the cushion to the boot at a selected position along the length of the slot.

The method for assembling, cleaning and using the preferred device is illustrated in Appendix A.

Having described my invention, I claim:

1. A medical boot, comprising:

a substantially boot-shaped main body (12) formed primarily of a substantially soft flexible, compressible, shape-retaining material, the boot body having a heel section and a leg-supporting section with a first fastener-receiving opening:

a rigid unitary splint formed separately from said boot body, said splint having a foot-support section, an elongated leg support section, and a heel section, the leg support section having a second fastener-receiving opening;

said splint being installable on the boot body so that the foot-support section of the splint is located within the boot body;

a cushion (16) receivable in the boot body for supporting the limb of a user, comprising:

an outer covering of substantially soft, flexible, compressible, shape-retaining material defining a main cushion portion;

an easily deformable, fluid-containing container disposed within the main cushion portion; and fastener means for releasably connecting the cushion (16) to the leg support section of the splint and the leg-supporting section of the main boot body (12) at such times as the fastener-receiving opening in the splint is aligned with the fastener-receiving opening in the leg-supporting section of the boot, at least one of said fastener-receiving openings comprising a slot parallel to the length of the leg-support section of the splint, said fastener means being disposed in said first fastener-receiving opening and the second fastener-receiving opening whereby the cushion is fastened an adjusted distance from the heel section of the boot body depending upon the longitudinal position of the fastener means in said slot.

2. A medical boot as defined in claim 1, in which said fastener means comprises:

a first fastener element carried on the cushion, and a second, complementary fastener element disposed outside the splint and the boot body, and engageable with the first fastener element to releasably lock the cushion to the splint and the boot body, at least one of the fastener elements being receivable in first fastener-receiving opening and the second fastener-receiving opening.

3. A medical boot as defined in claim 1, in which the main cushion portion has a generally rectangular configuration, and including a pair of side panels connected along opposite side edges of the main cushion portion by a linear fold line, each of the side panels having a configuration defined by the fold line, a second linear side edge forming an acute angle with and having one end intersecting the fold line, and a generally curved border continuing from the opposite end of the second linear side edge.

4. The medical boot of claim 1, in which the cushion including a pair of side panels extending from the main cushion portion, each side panel being foldable with respect to the main cushion portion.

5. A medical boot, comprising:
a substantially boot-shaped main body (12) formed primarily of a substantially soft flexible, compressible, shape-retaining material, the boot body having a heel section and an elongated leg-supporting section with a fastener-receiving slot (102) parallel to the length of the leg-supporting section, and a heel portion;
a cushion (16) receivable in the boot body for supporting the limb of a user, comprising:
an outer covering of substantially soft, flexible compressible, shape-retaining material defining a main cushion portion, and a pair of side panels extending from the main cushion portion, each side panel being foldable with respect to the main cushion portion;
an easily deformable, fluid-containing container disposed within the main cushion portion; and
fastener means for releasably connecting the cushion to the leg-supporting section of the boot an adjusted distance from the heel portion of the boot; said fastener means comprising:
a first fastener element carried on the cushion and a second complementary fastener element disposed outside the boot body, and engageable with the first fastener element to releasably lock the cushion to the boot body, at least one of the fastener elements being receivable in the fastener-receiving slot;
whereby the cushion is connected to the leg-supporting section of the boot body an adjusted distance from the heel portion thereof depending upon the longitudinal position of said at least one of the fastener elements in the fastener-receiving slot.

6. A medical boot as defined in claim 5, in which the main cushion portion has a generally rectangular configuration, and the pair of side panels connected along opposite side edges of the main cushion portion by linear fold line, each of the side panels having a configuration defined by the fold line, a second linear side edge forming an acute angle with and having one end intersecting the fold line, and a generally curved border continuing from the opposite end of the second linear side edge.

7. The medical boot of claim 5, in which the material is moleskin.

8. The medical boot of claim 5, in which the side panels are substantially symmetrical about the main cushion portion.

* * * * *